(12) United States Patent
Shirotani

(10) Patent No.: US 12,346,003 B2
(45) Date of Patent: Jul. 1, 2025

(54) PHOTOGRAPHY AID TOOL AND SKIN PHOTOGRAPHING DEVICE

(71) Applicant: IT Access CO., LTD, Kanagawa (JP)

(72) Inventor: Eiji Shirotani, Kanagawa (JP)

(73) Assignee: IT Access CO., LTD, Kanagawa (JP)

( * ) Notice: Subject to any disclaimer, the term of this patent is extended or adjusted under 35 U.S.C. 154(b) by 90 days.

(21) Appl. No.: 18/218,113

(22) Filed: Jul. 5, 2023

(65) Prior Publication Data
US 2024/0184184 A1     Jun. 6, 2024

Related U.S. Application Data

(63) Continuation of application No. PCT/JP2021/000128, filed on Jan. 5, 2021.

(51) Int. Cl.
*G03B 15/02*     (2021.01)
*A61B 5/00*      (2006.01)
*G03B 11/00*     (2021.01)

(52) U.S. Cl.
CPC ............ *G03B 15/02* (2013.01); *A61B 5/0077* (2013.01); *G03B 11/00* (2013.01)

(58) Field of Classification Search
CPC .............................. A61B 5/6898; A61B 5/441
See application file for complete search history.

(56) References Cited

U.S. PATENT DOCUMENTS 9,414,780 B2 * 8/2016 Rhoads ..................... G06T 5/40
9,427,187 B2    8/2016 Gilbert
10,405,752 B2 * 9/2019 Khosravi Simchi .........................
                                                       A61B 5/6898
2012/0172685 A1 * 7/2012 Gilbert ................. A61B 5/0077
                                                          600/306
2016/0192861 A1  7/2016 Gedeon et al.
2016/0248951 A1  8/2016 Fletcher et al.
2017/0199445 A1  7/2017 Endo et al.

(Continued)

FOREIGN PATENT DOCUMENTS

JP     2013257518     12/2013
JP     2016532512     10/2016

(Continued)

OTHER PUBLICATIONS

"Search Report of Europe Counterpart Application", issued on Feb. 20, 2024, p. 1-p. 7.

(Continued)

*Primary Examiner* — Leon W Rhodes, Jr.
(74) *Attorney, Agent, or Firm* — JCIPRNET

(57) ABSTRACT

Provided are a photography aid tool and a skin photographing device used for photographing skin. A main body is used for photographing skin with a portable device having a photographing device and an illumination device, and is composed of a front plate, a rear plate and a plurality of side plates. The main body has an insertion opening, a partition plate with two openings, and a portable device holder for holding the portable device. A polarizing filter is provided at the opening of the partition plate. The portable device is held by the portable device holder, and the skin photographing window of the front plate is in contact with the skin. The skin surface is photographed using only the light from the illumination device of the portable device while light outside the main body is blocked.

10 Claims, 14 Drawing Sheets

(56) References Cited

U.S. PATENT DOCUMENTS

2018/0140196 A1    5/2018  Khosravi Simchi et al.
2019/0281210 A1*   9/2019  Miyamoto ............. H04N 23/55

FOREIGN PATENT DOCUMENTS

WO    2019163373    8/2019
WO    2020162262    8/2020

OTHER PUBLICATIONS

"International Search Report (Form PCT/ISA/210) of PCT/JP2021/000128", mailed on Mar. 30, 2021, with English translation thereof, pp. 1-4.

"Written Opinion of the International Searching Authority (Form PCT/ISA/237) of PCT/JP2021/000128", mailed on Mar. 30, 2021, with English translation thereof, pp. 1-6.

* cited by examiner

PHOTOGRAPHY AID TOOL AND SKIN PHOTOGRAPHING DEVICE

CROSS-REFERENCE TO RELATED APPLICATION

This application is a continuation of the International PCT application serial no. PCT/JP2021/000128, filed on Jan. 5, 2021. The entirety of the above mentioned patent application is hereby incorporated by reference herein and made a part of this specification.

TECHNICAL FIELD

The present invention relates to a photography aid tool and a skin photographing device used for photographing skin.

BACKGROUND ART

As applications installed and executed on a smartphone, there is known an application that analyzes a condition of skin using image data of the skin photographed by a smartphone owned by a user. Among such applications, for example, as in Patent document 1, there is an application that is executed with attaching a dedicated attachment to a smartphone in order to perform highly accurate analysis.

PRIOR ART DOCUMENT

Patent Document

Patent document 1: JP2013-257518A

SUMMARY OF THE INVENTION

Problems to be Solved by the Invention

In many cases, the user's own skin analysis is done at the user's home. Analysis with the application can be easily performed by simply taking an image of the user's skin with a smartphone. In cases where skin analysis is routinely performed, it is desirable to use images photographed in the same photographing environment. However, with the so-called selfie-like photographing method, it is difficult to focus, to fix the position and angle of the smartphone camera for stable photographing, and to make the photographing area of the skin constant. There is also a problem that the lighting environment changes for each photographing because the time and location of photographing are different. These problems cause a decrease in analytical accuracy with the application.

Patent document 1 makes it possible to acquire images photographed in the same photographing environment by using a dedicated attachment. However, attachments such as Patent document 1, which include a photographic lens and lighting device for close-up photography, tend to be expensive, and users may be reluctant to introduce them from the viewpoint of cost. In addition, it is not only difficult for attachments with a specific shape to accommodate various smartphone shapes, but also there is the problem that smartphones are generally used with a case or cover, so the case or cover must be removed each time skin is photographed.

An object of the present invention is to provide a photography aid tool and a skin photographing device that are easy for users to implement and easy to photograph necessary images with using a smartphone application to analyze skin.

Means for Solving the Problems

The present invention is for solving the above problems, and an photography aid tool of the present invention, that is used to photograph a skin with a portable device having a photographing device and an illumination device and that has a main body composed of a front plate, a rear plate, and a plurality of side plates, comprises a skin photographing window, an insertion opening, a partition and a portable device holder. The main body forms a space inside by the front plate, the rear plate and the plurality of side plates. The skin photographing window is formed on the front plate. The partition is provided in parallel with the front plate inside the main body and has an opening for the photographing device and an opening for the illumination device that is provided in a position facing the skin photographing window. Through the insertion opening, the portable device is inserted into the main body. The portable device holder holds the inserted portable device in a space formed between the partition and the rear plate.

It is preferable that, on the partition, the opening for the photographing device is formed long in a direction perpendicular to an insertion direction of the portable device at a position farther from the insertion opening, and the opening for the illumination device is formed at a central part.

It is preferable to provide a photography polarizing filter for the photographing device and an illumination polarizing filter for the illumination device that is used to use a flash as polarized illumination light in a case where a display of the portable device functions as the flash. The photography polarizing filter is positioned to overlap the opening for the photographing device, and the illumination polarizing filter is positioned to overlap the opening for the illumination device.

It is preferable to provide a color palette inside the front plate in the main body, and the color palette is used to perform color correction and brightness correction of images photographed by the portable device.

It is preferable to provide an insertion guide used along with the portable device when inserting the portable device into the main body.

It is preferable to provide an attachment attached to the front plate side of the main body, and a sebum reactive sheet for measuring an amount of sebum on the skin is attached to the attachment.

A skin photographing device of the present invention comprises the photography aid tool, and it is preferable to photograph the skin surface by bringing a rim of the skin photographing window into contact with the skin, in a state where the portable device is held by the portable device holder.

It is preferable to photograph the skin surface using only the flash from the display in a light-shielded state in which light outside the main body is blocked by bringing the rim of the skin photographing window into contact with the skin.

It is preferable to provide at least two different photographing modes, and the photographing modes include a first photography mode using the photography polarizing filter and the illumination polarizing filter, and a second photography mode using only the photography polarizing filter.

It is preferable to operate in a third photographing mode using the photography polarizing filter and the illumination polarizing filter, in a state in which the portable device is held by the portable device holder and the attachment is attached to the main body.

Effect of the Invention

The photography aid tool and skin photographing device of the present invention can easily obtain necessary images when photographing skin using a smartphone application for skin analysis, which enables highly accurate analysis. In addition, since the structure is simple and the manufacturing cost is low, it can be provided to a user at low cost.

EMBODIMENTS OF THE INVENTION

First Embodiment

Figure 1:
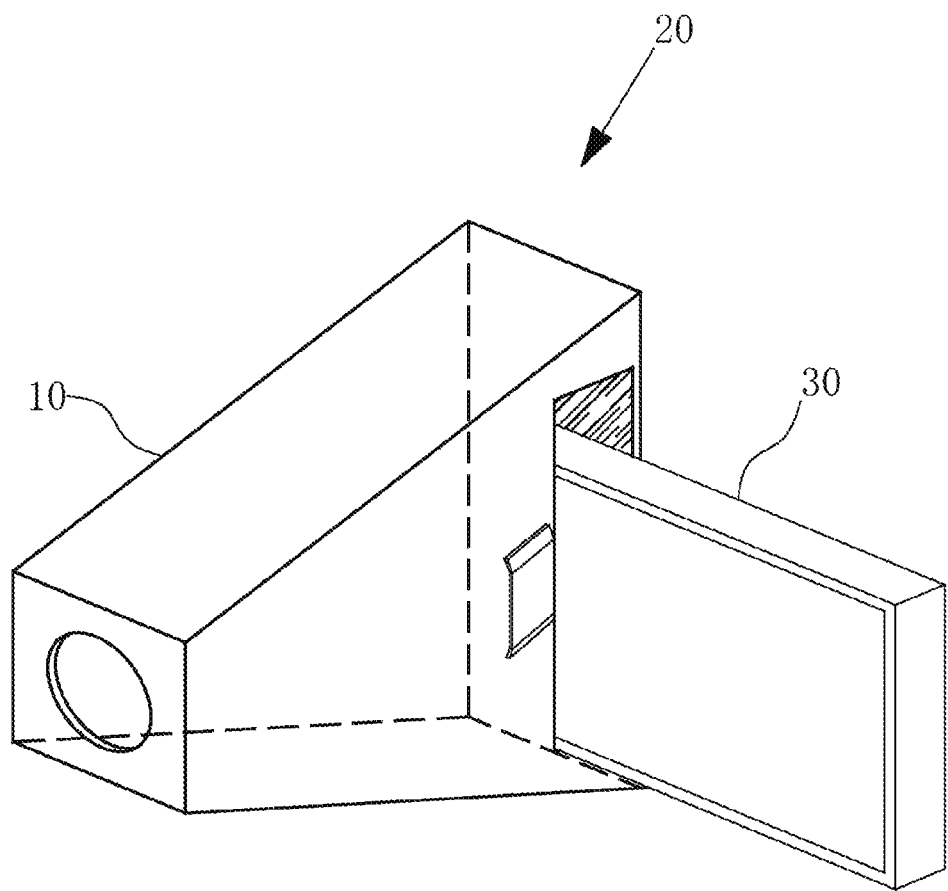
FIG. 1 is a perspective view of a skin photographing device using a photography aid tool of the present invention.

A photography aid tool 10 of the present invention is used with a smartphone (portable device) 30 owned by a user, as shown in FIG. 1, to photograph the user's own skin and to simply analyze the skin condition with a skin analysis application installed in the smartphone 30. The smartphone 30 in this specification also includes the smartphone 30 covered with a case or cover.

Figure 2:
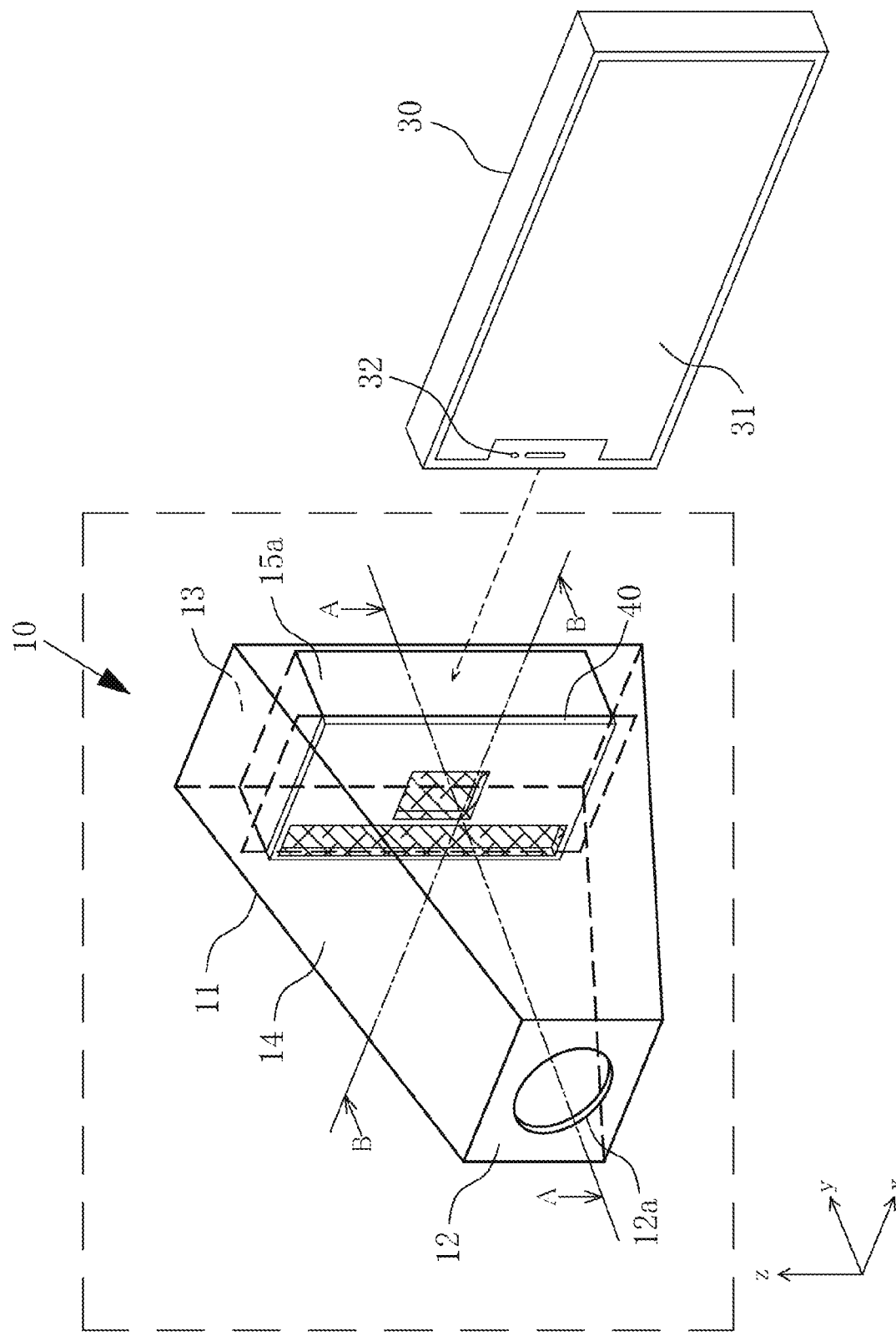
FIG. 2 is an external view showing the photography aid tool of the present invention.

As shown in FIG. 2, a main body 11, which forms the exterior of the photography aid tool 10, is composed of a front plate 12, a rear plate 13, and a plurality of side plates 14 connecting the front plate 12 and the rear plate 13, to form an interior space. The main body 11 is tapered along its longitudinal direction, tapering toward the front (in the direction of the front plate 12). The front plate 12 has a skin photographing window 12a hollowed out in a circular shape. A side surface of the main body 11 is formed with a smartphone insertion opening 15a for inserting the smartphone 30 inside the main body 11. As shown in FIG. 2, the direction indicated by the arrow x is the width direction of the photography aid tool 10 (insertion direction of the smartphone 30), similarly, the direction indicated by the arrow y is the longitudinal direction, and the direction indicated by the arrow z is the height direction.

Figure 3:
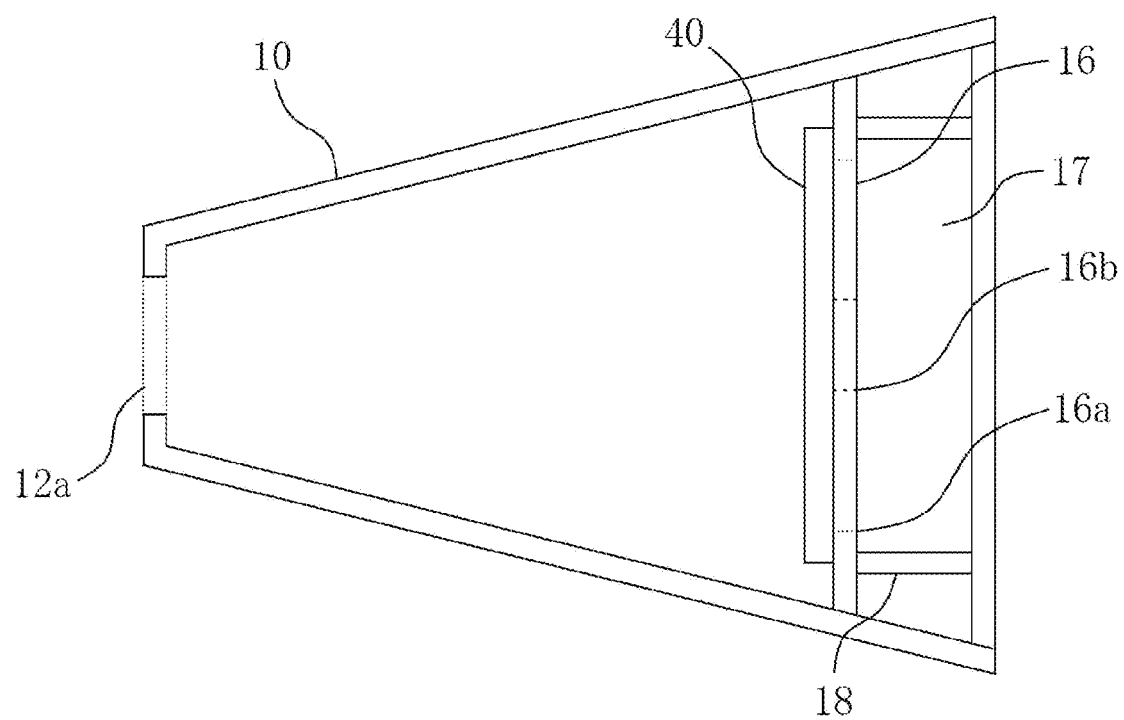
FIG. 3 is a schematic diagram showing the internal structure of the photography aid tool viewed from the width direction.

FIG. 3 schematically shows the internal structure of the main body 11. The main body 11 is provided with a partition plate 16 as shown in FIG. 3. The partition plate 16 is parallel to the front plate 12 and the rear plate 13. In addition, between the partition plate 16 and the rear plate 13, supporting members 18 are provided at the top and bottom to support the smartphone 30 in the center of the main body 11 of the photography aid tool 10 in the height direction when the smartphone 30 is inserted, so that the partition plate 16, the rear plate 13, and the top and bottom supporting members 18 form a smartphone holder (portable device holder) 17, a space for holding the smartphone 30. The smartphone 30 inserted through the smartphone insertion opening 15a is held in this space.

As for the dimensions of the photography aid tool 10, for example, the longitudinal dimension corresponding to the total length is about 70 to 140 mm. The front plate 12 is square with a side of about 50 mm, and the skin photographing window 12a in the center of the front plate 12 is circular with a diameter of about 30 mm. Also, the depth length (insertion direction dimension) of the smartphone holder 17 is about 60 mm. Inside the main body 11, the front plate 12 and the partition plate 16 are separated by a distance of about 50 to 120 mm. The smartphone insertion opening 15a is large enough to accommodate various forms of the smartphone 30, forming an opening with a width of about 20 mm and a height of about 90 mm. These dimensions may be arbitrarily determined according to variations in the form of the smartphone 30.

Figure 4:
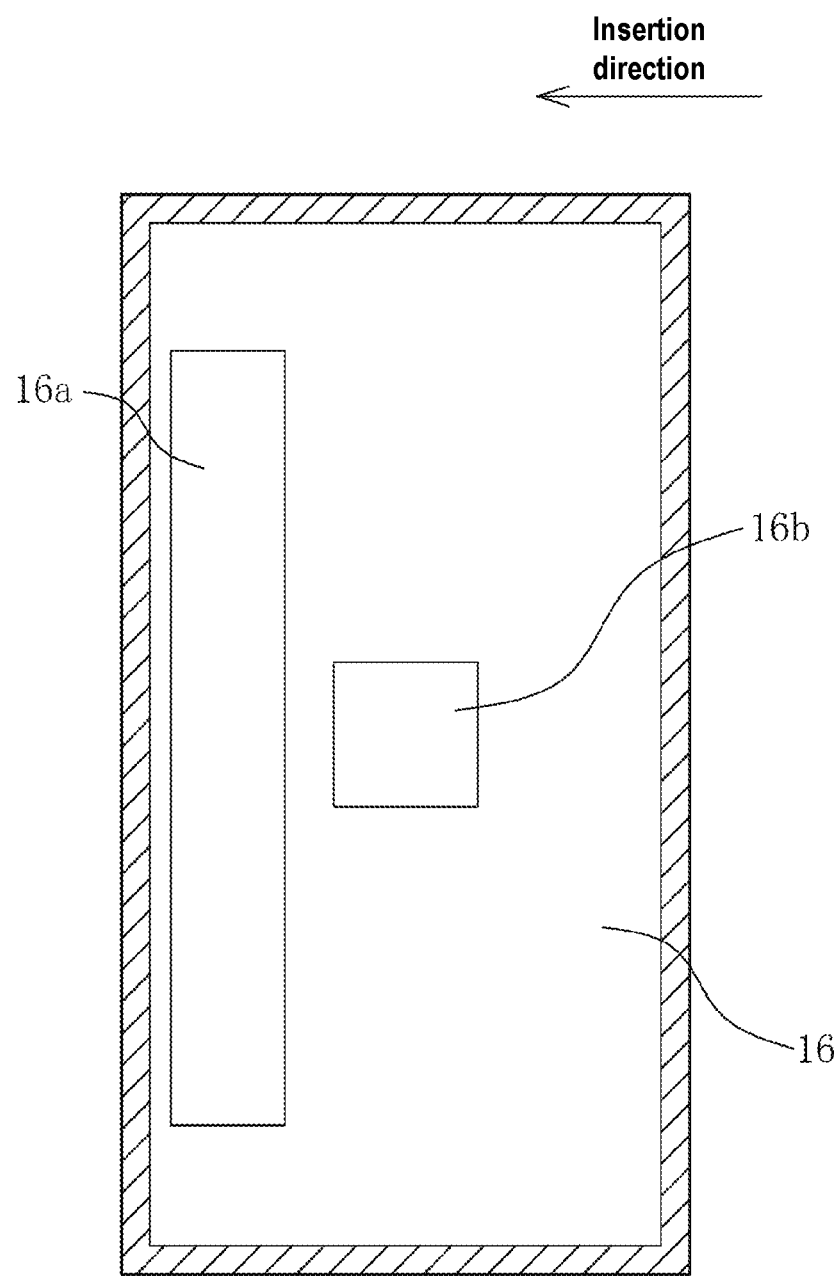
FIG. 4 is an explanatory diagram of a partition plate.

Some of the smartphones 30 in widespread use today have a pseudo flash function by making a display 31 emit brighter than usual when taking photographs with a front camera (see FIG. 2) 32 as a photographing device. In the present invention, this flash of the display 31 is used as an illumination device. As shown in FIG. 4, the partition plate 16 has an opening for photographing device 16a and an opening for illumination device 16b. The opening for photographing device 16a is formed in a long rectangular shape in a direction perpendicular to the insertion direction at a position farther from the smartphone insertion opening 15a into which the smartphone 30 is inserted. On the other hand, the opening for illumination device 16b is formed at a center of the partition plate 16 in a square shape with a side of about 15 mm. The mounting position of the front camera 32 of the smartphone 30 varies depending on the model in the horizontal direction, but in the vertical direction, in most cases, it is in the range of about 15 mm at the top, so the width of the opening is enough wide for many models. Also, the opening for illumination device 16b and the skin photographing window 12a are formed to face each other. Accordingly, when the main body 11 is viewed from the front, the opening for illumination device 16b appears to fit within the rim of the skin photographing window 12a.

As described above, the position and size of the opening for photographing device 16a is determined in consideration of the fact that the position of the front camera 32 of the smartphone 30 varies from model to model, allowing for a wide range of camera position differences to be absorbed when the smartphone 30 is inserted into the smartphone holder 17. Similarly, since the size of the display 31 of the smartphone 30 varies from model to model, the position and size of the opening for illumination device 16b is determined to illuminate the skin photographing window 12a from the opposite position, regardless of the model. In addition, the photography aid tool 10 has a symmetrical shape in order to enable photographing from the left and right directions, and the photography aid tool 10 can be used by flipping it upside down in the height direction. In this way, the skin photographing window 12a can be illuminated in the appropriate position or range, even when used inverted.

Figure 5A:
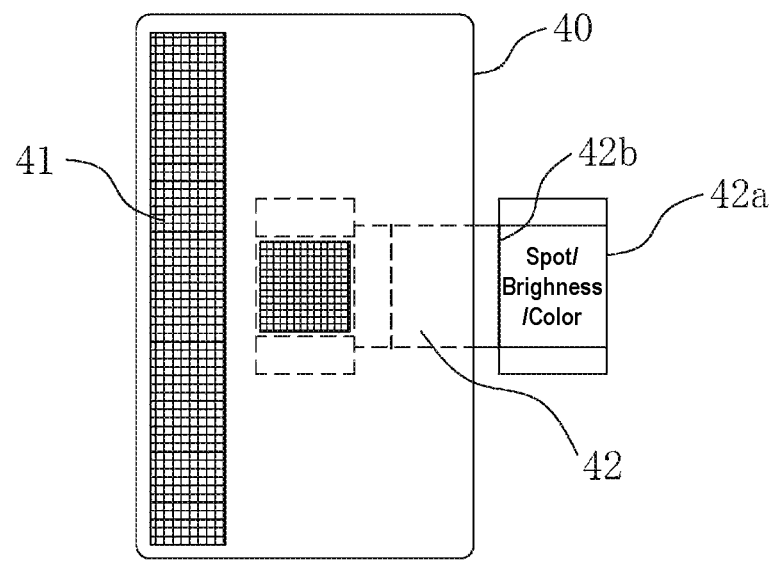
FIG. 5A is an explanatory diagram of a filter pad used in a first photographing mode.
Figure 5B:
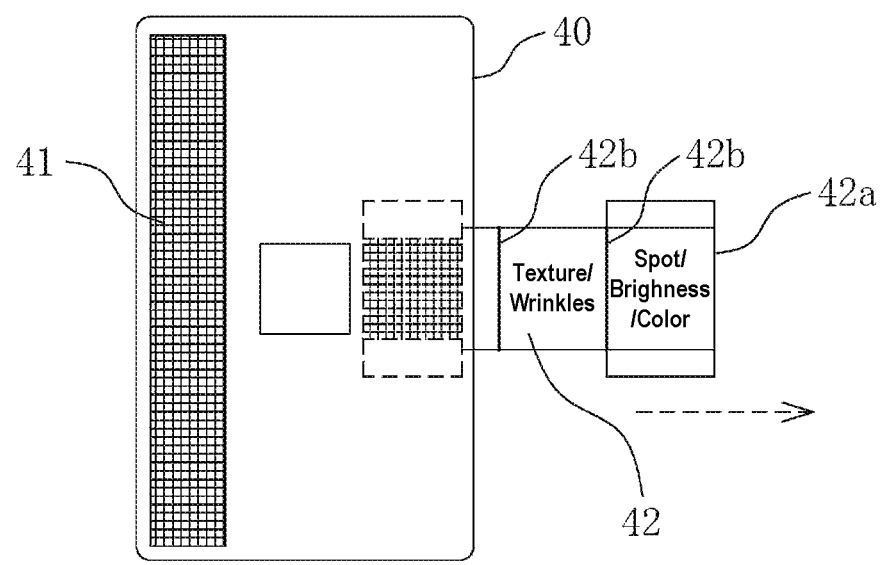
FIG. 5B is an explanatory diagram of a filter pad used in a second photographing mode.

Returning to FIG. 2, inside the main body 11 of the photography aid tool 10, a filter pad 40 adhered to the partition plate 16 is provided. As shown in FIGS. 5A and 5B, the filter pad 40 has a photography polarizing filter 41 for acquiring a polarized image with the front camera 32 of the smartphone 30, and an illumination polarizing filter 42 for using the flash of the display 31 of the smartphone 30 as polarized illumination light. Polarizing filter portions (not shown) of the photography polarizing filter 41 and the illumination polarizing filter 42 are arranged so that the polarization phase difference is 90 degrees. The photography polarizing filter 41 is fixed inside the filter pad 40, and the illumination polarizing filter 42 is enclosed so as to be movable along the direction of the arrow. The illumination polarizing filter 42 is T-shaped at both ends in the direction of movement, with the outer end serving as a stopper in the push-in direction and the inner end serving as a stopper in the pull-out direction, relative to the insertion direction. This allows the illumination polarizing filter 42 to move only within a determined range. The filter pad 40 is used in two forms according to photography modes. FIG. 5A shows a form used for non-reflection photography by suppressing the reflection of illumination light on the skin surface, and the photography polarizing filter 41 and the illumination polarizing filter 42 are applied to the filter pad 40. In the present invention, it is mainly used for spot/brightness/color photography (a first photographing mode) for analyzing skin spots, brightness, or color. On the other hand, FIG. 5B shows a form used for photographing the reflection of illumination light on the skin surface, in which only the photography polarizing filter 41 is applied to the filter pad 40 which is open in the center. This is mainly used to perform texture and wrinkle photography (a second photographing mode) to analyze skin texture or wrinkles. The polarizing filter portions of the photography polarizing filter 41 and the illumination polarizing filter 42 can be suitable for photographing images required for analysis, and the type, characteristics, or polarization direction of the polarizing filter portions can be determined as desired.

The illumination polarizing filter 42 is composed of the polarizing filter (not shown) and a tag 42a that allows the polarizing filter portion to move inside the filter pad 40. As shown in FIG. 5B, the tag 42a is provided with two section lines 42b. The position of the illumination polarizing filter 42 can be switched between the first and second photographing modes by using the section lines 42b as marks for aligning the position of the illumination polarizing filter 42, using the first section line for photographing spots, brightness, or color, and using the second line for photographing texture or wrinkles. In addition, the section line 42b has a crease and can be folded so as not to interfere with the operation of the display 31 of the smartphone 30.

Figure 6:
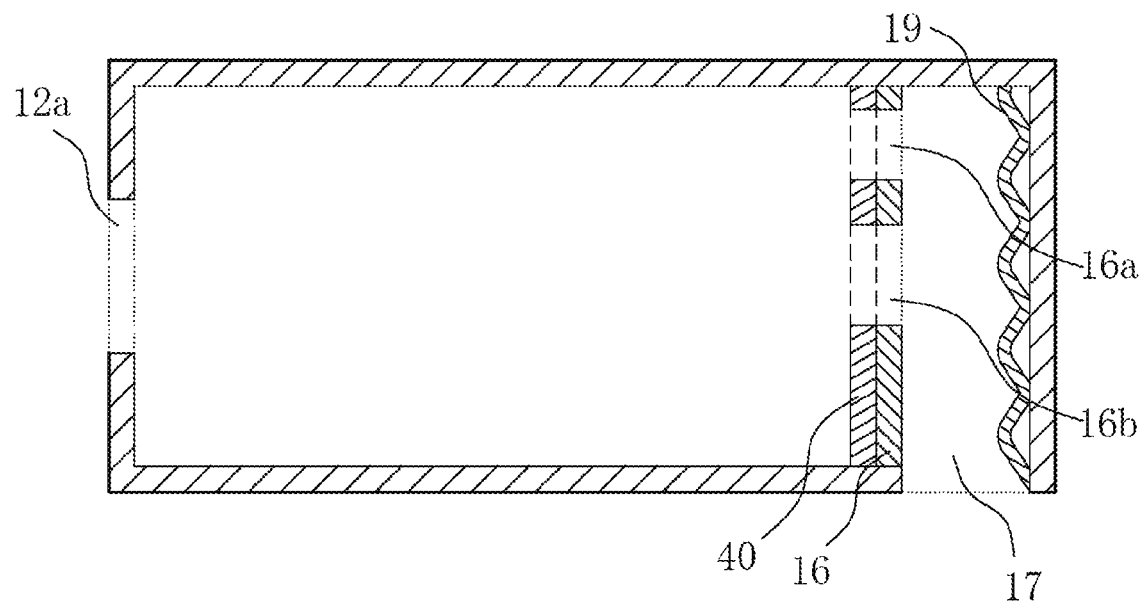
FIG. 6 is a cross-sectional view along a line A-A in FIG. 2.

FIG. 6 is a cross-sectional view along a line A-A in FIG. 2. A corrugated holder member 19 is provided on the rear plate 13 side to hold the smartphone 30 in the smartphone holder 17. The holder member 19 presses the smartphone 30 against the partition plate 16, so that the display 31 surface of the smartphone 30 and the partition plate 16 are flush with each other without any gap. Therefore, when photographing with a skin photographing device 20, which will be described later, the inner side surfaces of the openings of the partition plate 16 and the filter pad 40 are not photographed. The holder member 19 can adopt any shape, but it is preferable to adopt a shape with high resilience for repeated use in addition to high holding force. Also, as the holder member 19, a material such as elastic sponge may be used.

Figure 7:
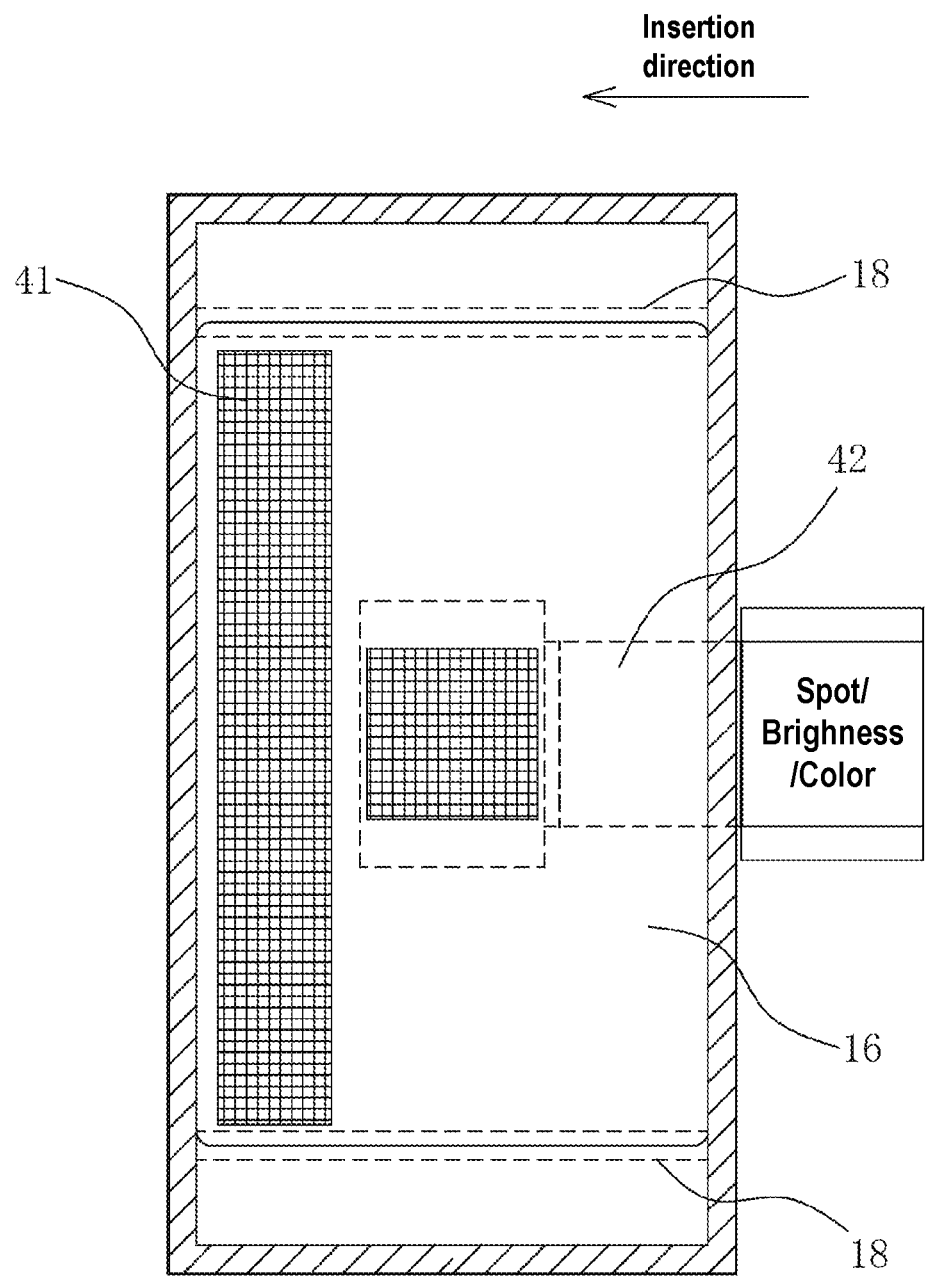
FIG. 7 is a cross-sectional view along a line B-B in FIG. 2.

FIG. 7 is a cross-sectional view along a line B-B in FIG. 2. As shown in FIG. 7, the polarizing filters of the filter pad 40 are adhered so as to overlap the positions of the openings of the partition plate 16. The photography polarizing filter 41 overlaps the opening for photographing device 16a, and the illumination polarizing filter 42 overlaps the opening for illumination device 16b. Note that FIG. 7 is an example of a case where spot/brightness/color photography is performed. Thus, the polarizing filter portions of the filter pad 40 are formed so that when the filter pad 40 is adhered to the partition plate 16, the entire surfaces of the corresponding openings are covered without gaps.

Figure 8:
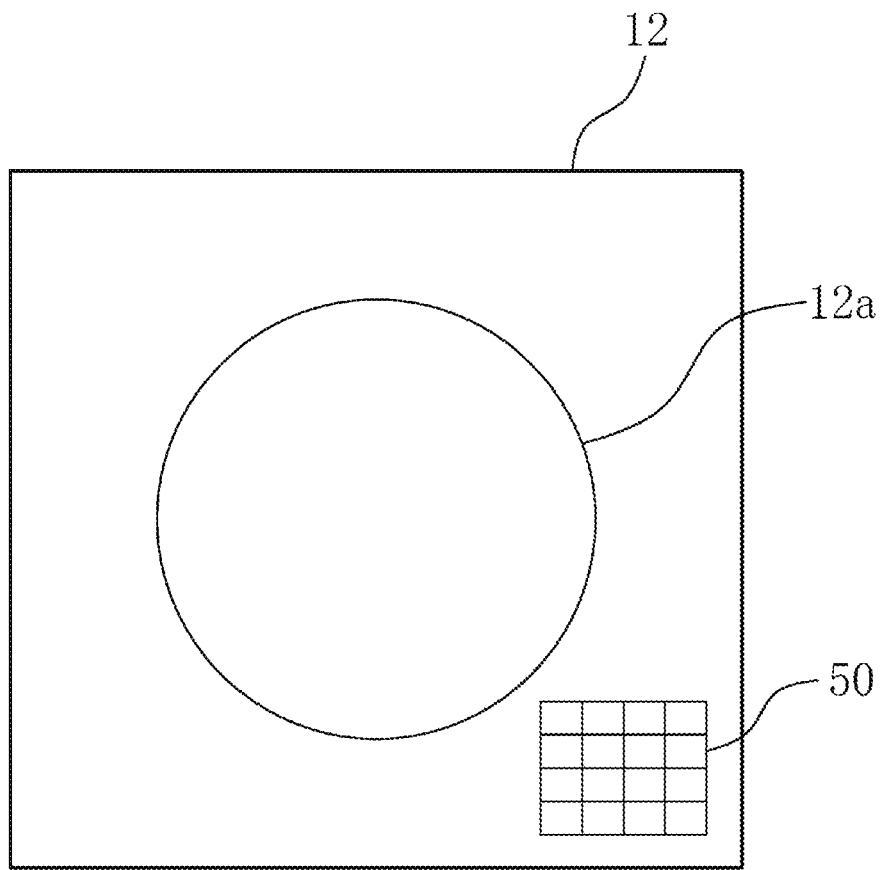
FIG. 8 is an explanatory diagram of a color palette provided on the front plate.

In addition, inside the front plate 12 of the photography aid tool 10, a color palette 50 is provided as shown in FIG. 8. The color palette 50 performs color correction/brightness correction of the photographed image by being photographed together with the skin. By providing the color palette 50, it is possible to reduce effects of color differences and brightness differences in photographed images caused by differences in a camera lens, an image sensor, a display that emits illumination light, etc., depending on the model of the smartphone 30.

Figure 9:
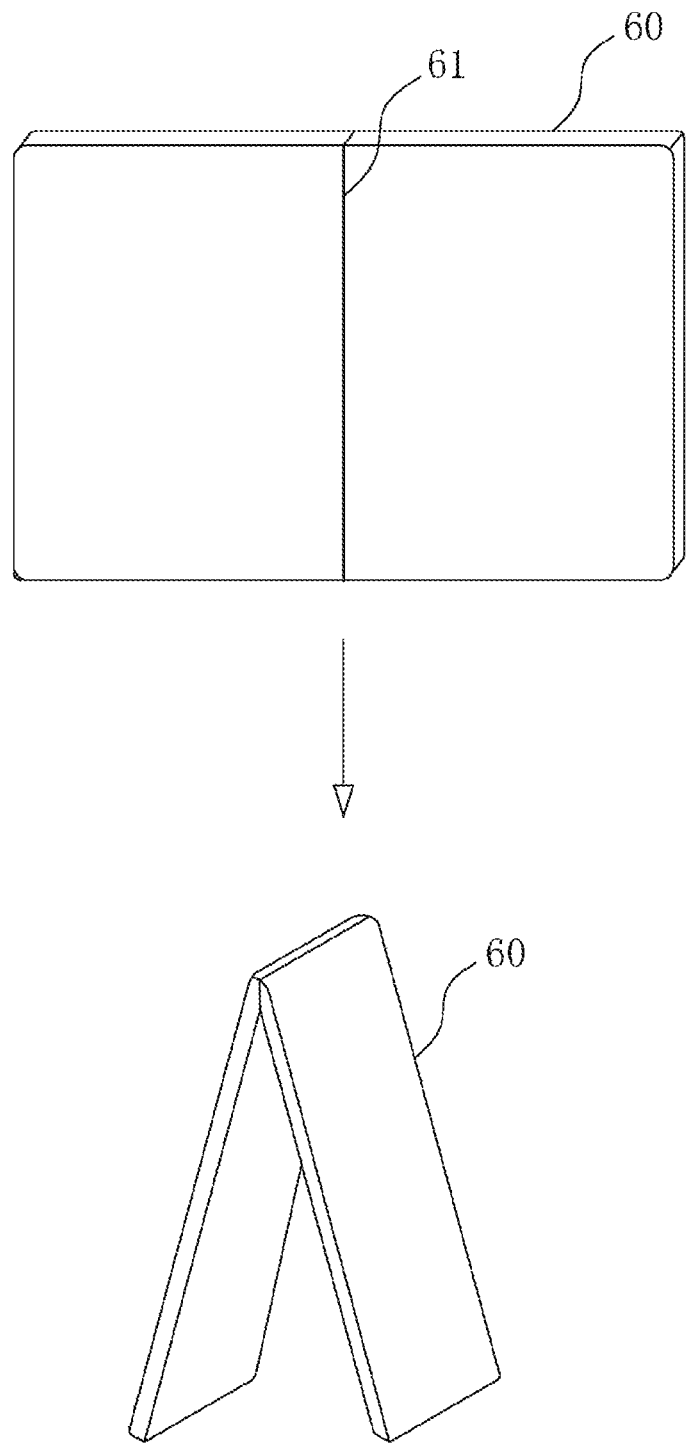
FIG. 9 is an explanatory diagram of an insertion guide.

Some models of the smartphone 30 have a step or unevenness on the back side. For example, there are those that use a case or cover with a card holder, those that have a retaining ring that holds the smartphone 30, and those that have unevenness due to decoration. In cases where the smartphone 30 has such a form, depending on the shape of the holder member 19 on the rear plate 13 side, the holder member 19 and the step or unevenness on the back side of the smartphone 30 may interfere with each other, making it difficult to insert and remove the smartphone 30 smoothly. To prevent such inconvenience, the photography aid tool 10 is provided with an insertion guide 60, as shown in FIG. 9. The insertion guide 60 is used along with the rear side of the smartphone 30 when inserting the smartphone 30 inside the main body 11. By providing the insertion guide 60, the photography aid tool 10 can be used according to various usage patterns of the smartphone 30 without any inconvenience. The insertion guide 60 is provided with a folding line 61 so that it can be folded in half from the central position. The longitudinal dimension of the insertion guide 60 is larger, even when folded, than the depth dimension of the smartphone holder 17. Accordingly, in case that the thickness of the smartphone 30 is thin, the holding force of the smartphone holder 17 can be increased by folding the insertion guide 60.

The inner surface of the main body 11 is painted black to reduce internal reflections by the illumination device. Alternatively, it may be painted in another dark color, and the main body 11 may be composed of a material close to black. That is, it is sufficient that the inner surface of the main body 11 has a structure that does not easily reflect light. In this way, the inner surface of the main body 11 is blackened to increase the light-shielding property of the main body 11, and also to reduce light reflected from the inner surface, which is an obstacle to skin analysis, allowing for highly accurate skin analysis.

As the material of each member that constitutes the photography aid tool 10, materials such as wood and metal can be appropriately used in addition to sheet-like materials such as cardboard made of paper or plastic. Also, a combination of those materials may be used. Of course, it is preferable to use a material with excellent workability from the viewpoint of manufacturing.

The main body 11 of the photography aid tool 10 has a tapered front portion, but may have other structures. For example, a rectangular parallelepiped structure, which can be manufactured more easily, or a user-friendly structure, such as a cylindrical body or a triangular body, can be used. In other words, any shape can be used as long as the structure can hold the skin photographing window 12a and the smartphone 30 in parallel and keep the photographing distance constant.

Second Embodiment

Returning to FIGS. 1 and 2, a case of using the photography aid tool 10 of the first embodiment as the skin photographing device 20 will be described. As shown in FIGS. 1 and 2, the skin photographing device 20 is used in a state where the smartphone 30 is inserted inside the main body 11 of the photography aid tool 10 and the smartphone 30 is held by the smartphone holder 17 (use state). In the use state, the skin photographing device 20 photographs the skin surface by pressing the front plate 12 against the skin. Accordingly, when photographing, the inside of the main body 11 of the photography aid tool 10 becomes a light-shielded state that blocks the light outside the main body 11, the flash of the display 31 of the smartphone 30, which is the illumination light, illuminates the skin in the skin photographing window 12a through the opening for illumination device 16b, and only the light reflected by the surface of the skin or the superficial layer of the skin enters the front camera 32 of the smartphone 30 through the opening for photographing device 16a. Since photographing with the skin photographing device 20 is done in contact with the skin so that ambient light, which is light outside the photography aid tool 10, does not enter the interior of the photography aid tool 10, it is possible to prevent unnecessary light other than the light from the display 31 from being photographed by the front camera 32. Then the skin analysis application of the smartphone 30 uses the image data thus photographed to perform analysis corresponding to the photography mode.

For a more detailed use of the skin photographing device 20, in case the user wants to know the condition of spots, brightness, or color of the skin by the skin analysis application of the smartphone 30, the first photographing mode is executed after setting the filter pad 40 of the photography aid tool 10 to the state shown in FIG. 5A. Also, in case the user wants to know the condition of skin texture or wrinkles, the second photographing mode is executed after setting the filter pad 40 of the photography aid tool 10 to the state shown in FIG. 5B. The skin analysis application uses a different image for each photography mode and analyzes the skin corresponding to the photography mode. In the first photography mode, the non-reflection photography is performed by irradiating the skin of the face with polarized illumination light polarized in a certain direction, to analyze the brightness of the skin surface and the condition of spots, brightness, and color caused by pigments contained in the skin surface layer. In addition, in the second photography mode, the state of texture and wrinkles is analyzed by irradiating illumination light that does not pass through the polarizing filter and photographing the degree of reflection of illumination light caused by fine irregularities on the skin surface. The skin analysis by the skin analysis application of the smartphone 30 can be performed, for example, by a known method described in JPH03-125322U.

As described above, the skin photographing device 20 of the present invention photographs images of the skin for skin analysis using only the necessary illumination light while the photographing space is shielded from outside light, and the image data obtained in this manner is used for the analysis. Therefore, even if the time and location for photographing differs, the photographing environment does not change for each photographing, and highly accurate analysis can be performed. The user can then use the results of the analysis by the skin photographing device 20 to manage the skin in daily life and select cosmetics in a meaningful way.

In addition, the main body 11 of the photography aid tool 10 is made symmetrical, so it is easy to use the skin photographing device 20 to photograph the skin on either side of the face, and the orientation of the photographing device 20 can be selected according to the user's preference and dominant hand.

Note that the skin photographing device 20 can be used not only for facial skin but also for other parts of the body. For example, by using the skin photographing device 20 on the head, arms, etc., it is possible to analyze the skin surface of the photographed part. Since the skin photographing device 20 of the present invention can maintain a constant photographing distance and photographing area, even in a case where direct operation on the display 31 is difficult, for example when photographing the head for the scalp, it is easy to photograph necessary images by timer photographing function of the application side.

Note that instead of analysis by the skin analysis application on the smartphone 30, the images photographed by the skin photographing device 20 may be sent to a server such as a cloud, and a program for skin analysis may be executed on the cloud.

Third Embodiment

Figure 10:
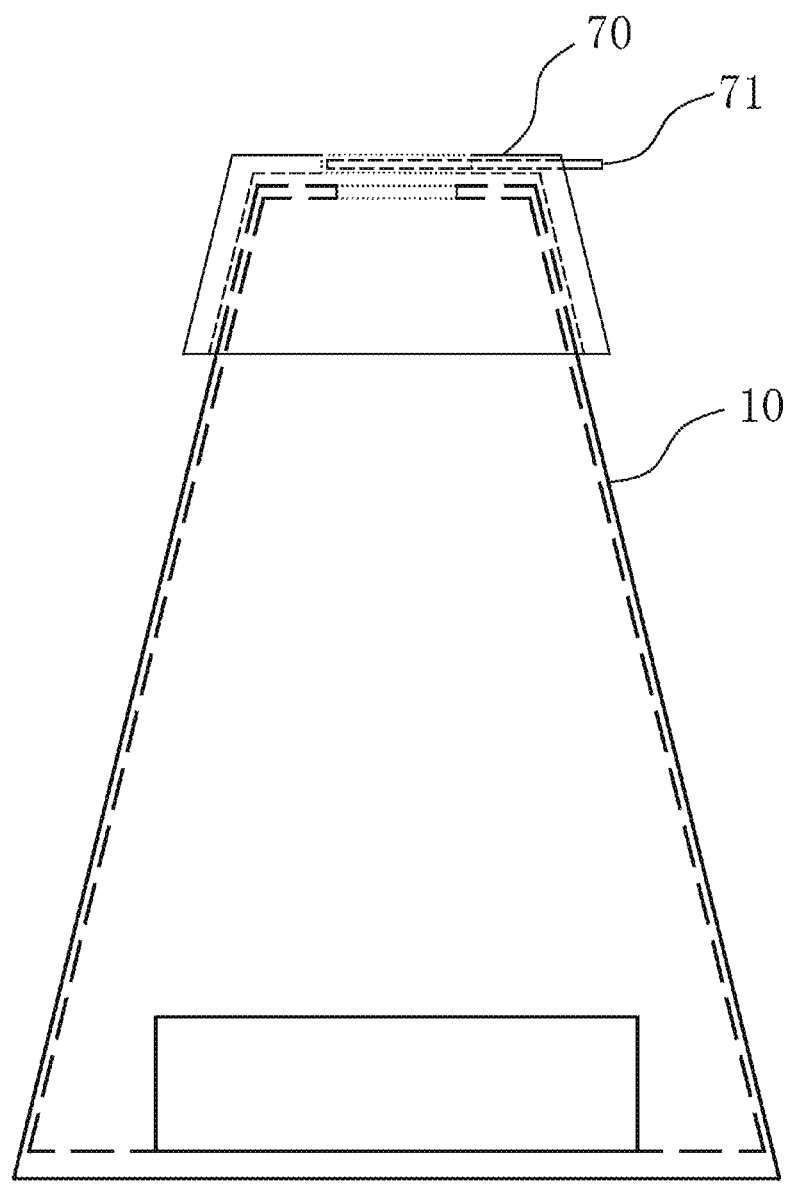
FIG. 10 is an explanatory diagram of an attachment used in a third photography mode.
Figure 11:
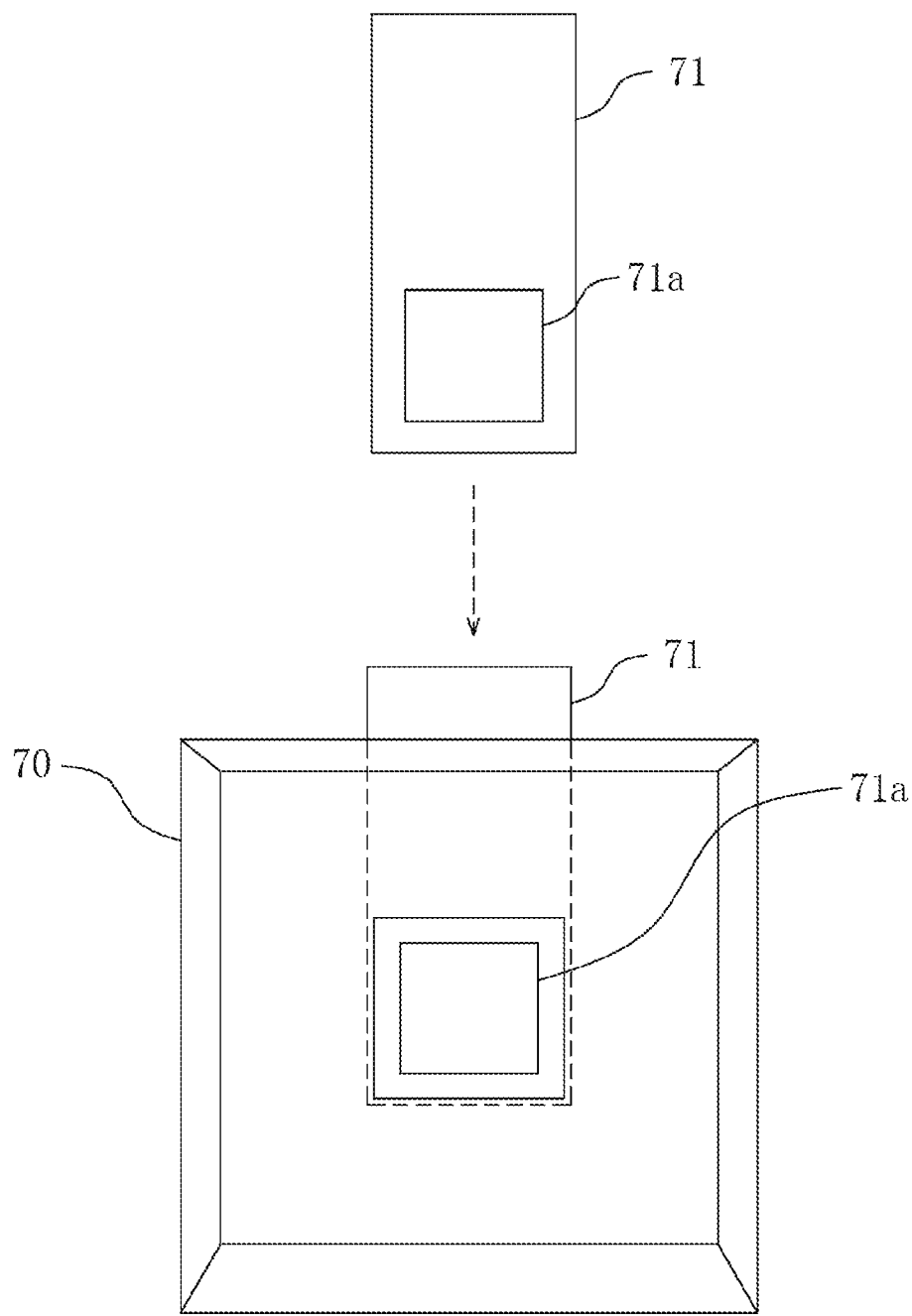
FIG. 11 is an explanatory diagram of the attachment viewed from the inside.

The skin photographing device 20 of the third embodiment is different from the skin photographing device 20 of the second embodiment, and performs sebum photography (a third photography mode) to analyze the amount of sebum in the skin, with attaching an attachment 70 to the photography aid tool 10 as shown in FIG. 10. As shown in FIGS. 10 and 11, the attachment 70 is formed like a cap along the shape of the tip of the main body 11. In addition, the attachment 70 has a sebum reactive sheet 71 that is used by being inserted into an insertion section (not shown) on the front part of the attachment 70. The sebum reactive sheet 71 is used by attaching it to the attachment 70 when performing the third photography mode. The inner surface of the front part of the attachment 70 has an opening at the center so that a sebum reactive section 71a of the sebum reactive sheet 71 is exposed when the sebum reactive sheet 71 is attached. In the third photographing mode, the sebum reactive section 71a of the sebum reactive sheet 71 exposed on the inner surface of the front part of the attachment 70 is photographed when the attachment 70 with the sebum reactive sheet 71 is placed on the main body 11. The insertion section of the attachment 70 has a so-called pocket-like shape as a whole, so that when the sebum reactive sheet 71 is inserted, the sebum reactive section 71a is positioned exactly in the center. In addition, since the width of the insertion section is formed slightly wider than the width of the sebum reactive sheet 71, and the inner surface of the insertion section in the width direction serves as a guide when inserting the sebum reactive sheet 71, the sebum reactive sheet 71 can be inserted smoothly.

Specifically, the user brings the sebum reactive sheet 71 into contact with the skin for a few seconds before executing the third photographing mode on the smartphone 30 application, and attaches the sebum reactive sheet 71 to the attachment 70 after confirming that the sebum reactive sheet 71 reacts to the sebum of the skin and changes color. Then, the tip of the photography aid tool 10 is covered with the attachment 70, and the skin analysis application of the smartphone 30 executes the third photography mode, which is a non-reflective photography similar to the first photography mode. As a result, the sebum reactive section 71a of the sebum reactive sheet 71 is photographed with reduced surface reflection, and the amount of sebum can be analyzed based on the photographed image. In the third embodiment of the skin photographing device 20, by placing the cap-like attachment 70 on the photography aid tool 10, the interior of the photography aid tool 10 is light-shielded as in the second embodiment of the skin photographing device 20, thus it is possible to accurately analyze the amount of sebum without photographing unnecessary light other than the light from the display 31.

Fourth Embodiment

Figure 12:
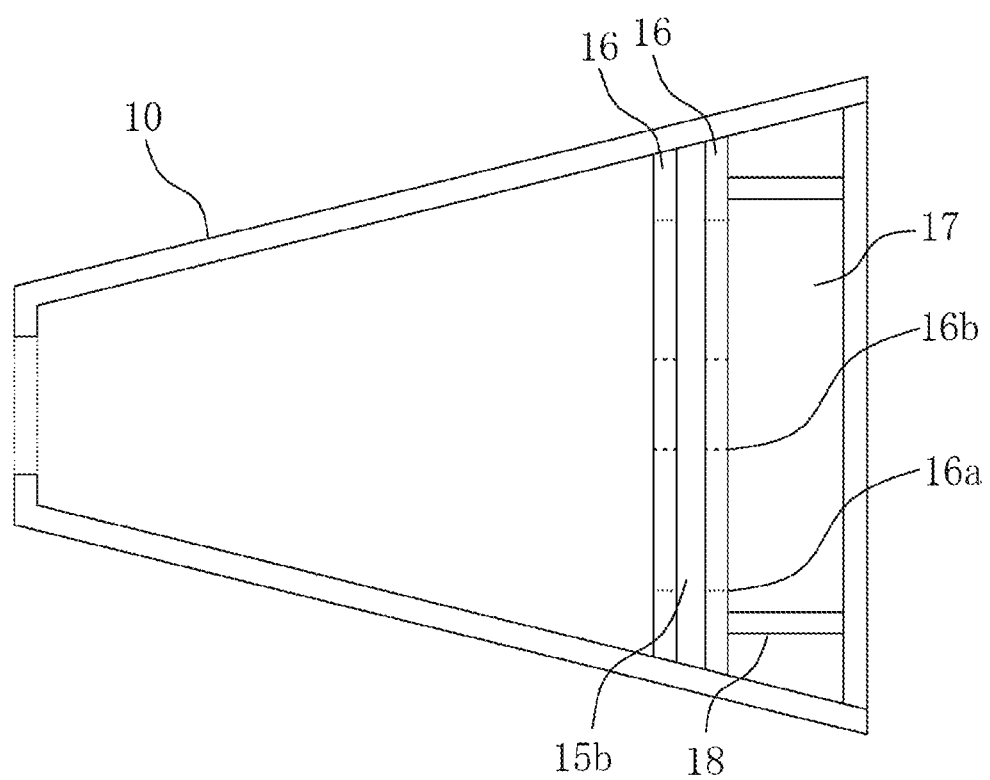
FIG. 12 is a schematic diagram showing an internal structure with two partition plates.
Figure 13A:
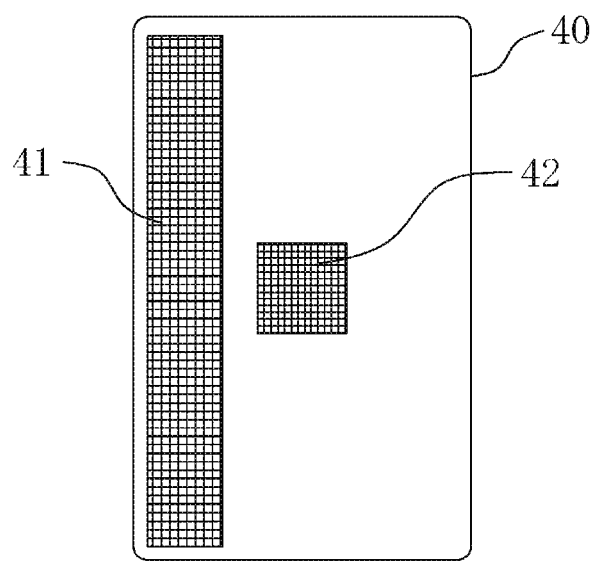
FIGS. 13A and 13B are explanatory diagrams showing another embodiment of the filter pad.
Figure 13B:
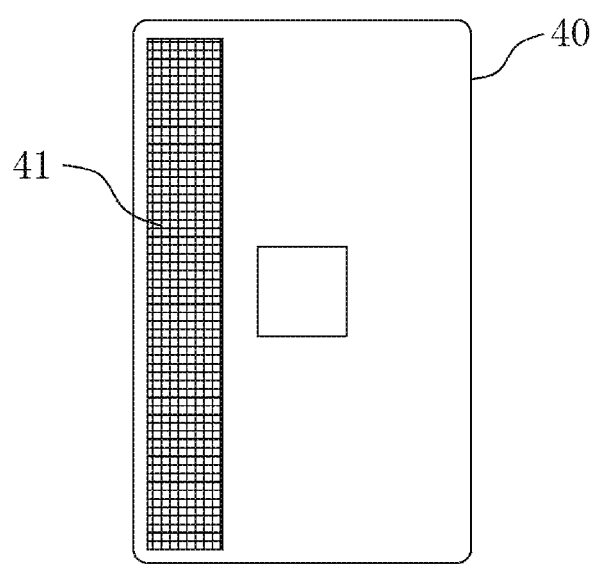

In the above embodiments, one partition plate 16 is used to constitute the smartphone holder 17 with the rear plate 13, but in the fourth embodiment shown in FIG. 12, there are two partition plates 16. In FIG. 12, two partition plates 16 of the same shape form a partition, and the partition plates 16 are arranged parallel to each other to form a narrow space. The filter pad 40 is detachably stored in this space. Also, the opening for photographing device 16a and the opening for illumination device 16b of each one of the partition plates 16 are formed at positions facing the openings of the other partition plate, constituting openings of the two partition plates 16. In this embodiment, as shown in FIGS. 13A and 13B, two different filter pads 40 are used. One shown in FIG. 13A is used in the first photography mode, and incorporates the photography polarizing filter 41 and the illumination polarizing filter 42. One shown in FIG. 13B is used in the second photographing mode, incorporates the photography polarizing filter 41, and has an opening in the center.

Figure 14:
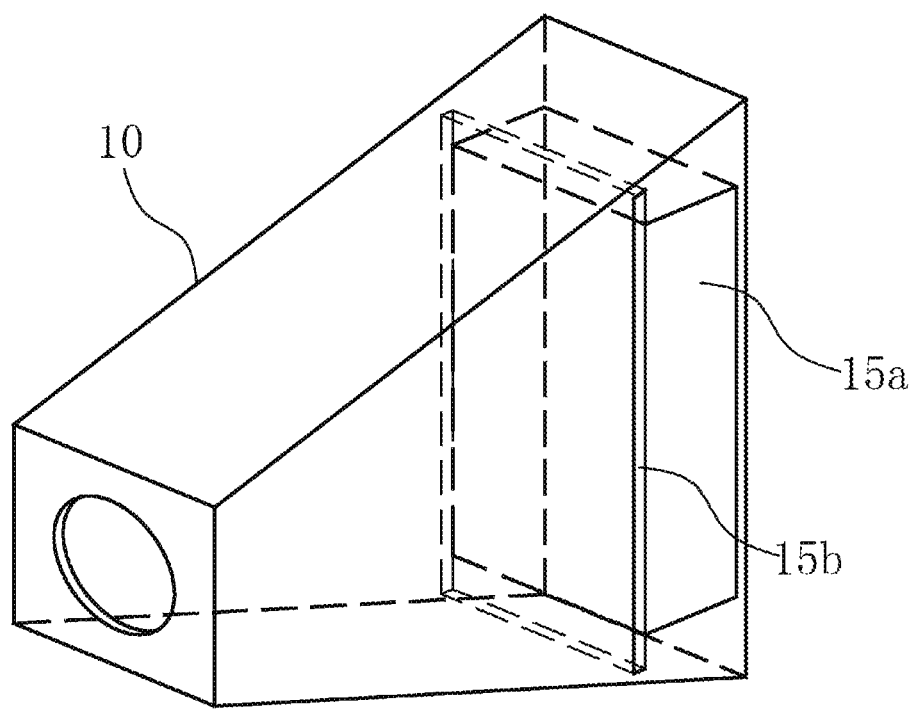
FIG. 14 is an explanatory diagram of a filter pad insertion opening.

Further, as shown in FIG. 14, a filter pad insertion opening 15b for inserting the filter pad 40 is formed on the side surface of the main body 11 of the photography aid tool 10 of this embodiment. Although not shown in FIGS. 13A and 13B, the filter pad insertion opening 15b is provided with a cover to prevent external light from entering. When using the skin photographing device 20, the user switches the filter pad 40 between the first and second photographing modes, and the filter pad 40 corresponding to the photographing mode is inserted inside the main body 11 of the photography aid tool 10.

Although the photography aid tool 10 and the skin photographing device 20 of each of the above embodiments are configured to use the front camera 32 of the smartphone 30, a configuration using a rear camera (not shown) of the smartphone 30 may be used. The rear camera of the smartphone 30 generally has higher performance than the front camera 32, so using the rear camera has the advantage of being able to perform highly accurate skin analysis using high-quality images. In this case, it is desirable to provide the filter pad 40 different from the filter pad 40 of each of the above embodiments in order to accommodate various models of the smartphone 30.

In each of the above embodiments, the smartphone 30 is used for the skin photographing device 20, but a terminal such as a tablet may be used as long as it has the same functions as the smartphone 30 described in this specification. Since the photography aid tool 10 has a simple structure and can be easily manufactured in any size, it can be manufactured according to the size of the tablet. In this case as well, the skin photographing device 20 has the same necessary functions as in the above embodiments, so that photography for skin analysis can be easily performed.

Each member of the photography aid tool 10 may be joined together by adhesive or other materials as described above, or may have an assembly structure that can be partially disassembled. In case it has an assembly structure that can be stored compactly, for example, it can be used even at a place of visit, so that the user can use the skin photography device 20 of the present invention on a daily basis without fail to manage the skin condition.

What is claimed is:

1. A photography aid tool that is used to photograph a skin with a portable device having a photographing device and an illumination device, and that has a main body composed of a front plate, a rear plate, and a plurality of side plates, the photography aid tool comprising:
   a skin photographing window formed on the front plate;
   an insertion opening through which the portable device is inserted into a space formed inside the main body, wherein a width of the insertion opening is greater than a width of the portable device;
   a portable device holder holding the inserted portable device in a space formed between a partition and the rear plate, the partition provided in parallel with the front plate inside the main body and having an opening for the photographing device and an opening for the illumination device, the opening for the illumination device being provided in a position facing the skin photographing window.

2. The photography aid tool according to claim 1, wherein on the partition,
   the opening for the photographing device is formed long in a direction perpendicular to an insertion direction of the portable device at a position farther from the insertion opening, and
   the opening for the illumination device is formed at a central part.

3. The photography aid tool according to claim 2, further comprising:
   a photography polarizing filter for the photographing device; and
   an illumination polarizing filter for the illumination device, that is used to use a flash as polarized illumination light in a case where a display of the portable device functions as the flash,
   wherein the photography polarizing filter is positioned to overlap the opening for the photographing device, and
   the illumination polarizing filter is positioned to overlap the opening for the illumination device.

4. The photography aid tool according to claim 3, further comprising:
   a color palette that is provided inside the front plate in the main body, and is used to perform color correction and brightness correction of images photographed by the portable device.

5. The photography aid tool according to claim 3, further comprising:
an insertion guide used along with the portable device when inserting the portable device into the main body.

6. The photography aid tool according to claim 3, further comprising:
an attachment attached to the front plate side of the main body,
wherein a sebum reactive sheet for measuring an amount of sebum on the skin is attached to the attachment.

7. A skin photographing device comprising the photography aid tool according to claim 3, wherein the skin photographing device is configured to photograph the skin surface by bringing a rim of the skin photographing window into contact with the skin, in a state where the portable device is held by the portable device holder.

8. The skin photographing device according to claim 7, wherein the skin photographing device is configured to photograph the skin surface using only the flash from the display in a light-shielded state in which light outside the main body is blocked by bringing the rim of the skin photographing window into contact with the skin.

9. The skin photographing device according to claim 7, wherein the skin photographing device is configured to photograph through at least two different photographing modes, and
wherein the at least two different photographing modes include a first photography mode using the photography polarizing filter and the illumination polarizing filter and a second photography mode using only the photography polarizing filter.

10. A skin photographing device comprising the photography aid tool according to claim 6, and operating in a third photographing mode using the photography polarizing filter and the illumination polarizing filter, in a state in which the portable device is held by the portable device holder and the attachment is attached to the main body.

* * * * *